United States Patent [19]

Marhold

[11] Patent Number: 4,783,562

[45] Date of Patent: Nov. 8, 1988

[54] PROCESS FOR THE PREPARATION OF TRICHLOROMETHYL-SUBSTITUTED AROMATIC COMPOUNDS, AND TRICHLOROMETHYL-SUBSTITUTED AROMATIC COMPOUNDS OBTAINED IN THIS PROCESS

[75] Inventor: Albrecht Marhold, Leverkusen, Fed. Rep. of Germany

[73] Assignee: Bayer Aktiengesellschaft, Leverkusen, Fed. Rep. of Germany

[21] Appl. No.: 352,494

[22] Filed: Feb. 25, 1982

[30] Foreign Application Priority Data

Mar. 14, 1981 [DE] Fed. Rep. of Germany ....... 3109966

[51] Int. Cl.$^4$ ............ C07C 17/22; C07C 21/24
[52] U.S. Cl. ........................................... 570/196
[58] Field of Search ............ 570/185, 183, 184, 127, 570/129, 196, 197, 198, 191, 201, 140, 141, 142, 144, 145, 147; 260/465 G; 204/163 R

[56] References Cited

U.S. PATENT DOCUMENTS

| | | | |
|---|---|---|---|
| 2,005,712 | 6/1935 | Holt et al. | 570/127 |
| 2,957,001 | 10/1960 | Smith | 570/140 |
| 3,084,203 | 4/1963 | LeSuer et al. | 570/184 |
| 3,278,552 | 10/1966 | Geering | 570/185 |
| 4,038,331 | 7/1977 | Tobin | 570/144 |
| 4,049,708 | 9/1977 | Kollonitsch et al. | 570/140 |
| 4,056,455 | 11/1977 | Lademann et al. | 204/163 R |
| 4,155,940 | 5/1979 | Marhold et al. | 570/127 |
| 4,226,783 | 10/1980 | Marsh | 570/196 |
| 4,242,286 | 12/1980 | Ohsaka | 260/465 G |
| 4,306,102 | 12/1981 | Landauer et al. | 570/185 |
| 4,331,613 | 5/1982 | Marhold et al. | 570/129 |
| 4,334,111 | 6/1982 | Davis et al. | 570/144 |

FOREIGN PATENT DOCUMENTS

| | | | |
|---|---|---|---|
| 8453 | 3/1980 | European Pat. Off. | 570/127 |
| 1815452 | 7/1969 | Fed. Rep. of Germany . | |
| 59645 | 5/1978 | Japan | 260/465 G |

OTHER PUBLICATIONS

Reid, *Organic Chemistry of Bivalent Sulfur*, vol. VI, (1966), QD412.S1,R4,C2.

*Primary Examiner*—Werren B. Lone
*Attorney, Agent, or Firm*—Sprung Horn Kramer & Woods

[57] ABSTRACT

Trichloromethyl-substituted aromatic compounds are obtained by the chlorination of thioethers of the formula

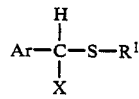

wherein
Ar represents an optionally substituted aryl radial,
$X_1$ denotes hydrogen or halogen, and
$R^1$ represents optionally substituted alkyl, aralkyl, the nitrile group, an optionally substituted aryl radical or the group

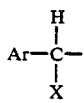

wherein Ar and X have the meaning given.

The compounds, of which some are new, can be used as intermediate products for plant protection agents.

6 Claims, No Drawings

PROCESS FOR THE PREPARATION OF TRICHLOROMETHYL-SUBSTITUTED AROMATIC COMPOUNDS, AND TRICHLOROMETHYL-SUBSTITUTED AROMATIC COMPOUNDS OBTAINED IN THIS PROCESS

The invention relates to a process for the preparation of trichloromethyl-substituted aromatic compounds, and trichloromethyl-substituted aromatic compounds obtained in this process.

The preparation of trichloromethyl-substituted aromatic compounds by chlorination of the side-chain of methyl-substituted aromatic compounds is known. Thus, for example, benzotrichloride can be prepared by chlorination of the side-chain of toluene (Houben-Weyl-Müller VI, Volume 3, 4th edition, 1962, page 738).

Methyl-substituted aromatic compounds which also contain other substituents, for example alkyl groups, alkoxy groups, halogens and nitro groups, cannot be chlorinated in this manner to give trichloromethyl-substituted aromatic compounds, because these substituents either react with chlorine themselves or prevent chlorination of the methyl group. Thus, for example, methylbenzotrichloride can only be prepared by chlorination of methylbenzothiocarboxylic acid-chloride (R. Meyer, S. Scheitauer, Chem. Ber. Volume 98, page 829).

This reaction has the disadvantage that the thiocarboxylic acid-chlorides required in the process are not readily accessible.

A process for the preparation of trichloromethyl-substituted aromatic compounds of the formula

     (I)

wherein

Ar represents an optionally substituted aryl radical, has been found, which is characterised in that thioethers of the formula

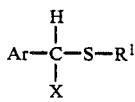     (II)

wherein

Ar has the meaning given above,

X denotes hydroen or halogen, and

R¹ represents an optionally substituted aryl radical, the group

wherein

Ar and X have the meaning given above, optionally substituted alkyl, aralkyl or the nitrile group,
are reacted with a chlorinating agent, if desired in a solvent, in the temperature range of from −20° to 125° C.

Radicals having 6 to 14 C atoms, such as phenyl, naphthyl and anthryl, may be mentioned as examples of aryl. The phenyl radical and naphthyl radical are preferred.

Straight-chain or branched radicals having 1 to about 8 C atoms, preferably a lower alkyl radical (1 to about 4 carbon atoms), such as methyl, ethyl, propyl, isopropyl, butyl, isobutyl, hexyl, octyl and isooctyl, may be mentioned as examples of alkyl. Methyl, ethyl, propyl, isopropyl, butyl and hexyl are preferred, and methyl, ethyl, propyl and butyl are particularly preferred.

Radicals having 6 to 14 C atoms in the aryl part and 1 to 4 C atoms in the alkyl part, such as benzyl, 1-naphthylmethyl, 2-naphthylmethyl, 1-anthrylmethyl, 2-anthrylmethyl, 9-anthrylmethyl, phenylethyl, 1-naphthylethyl; 2-naphthylethyl, 1-anthrylethyl, 9-anthrylethyl, phenylpropyl, phenyl-isopropyl, 1-naphthylpropyl, 1-naphthylisopropyl, phenylbutyl, phenyl-2-butyl, 1-naphthylbutyl, 1-naphthyl-2-butyl, 2-naphthyl-1-butyl and 2-naphthyl-2-butyl, may be mentioned as examples of aralkyl. Radicals having 6 to 10 C atoms in the aryl part and 1 to 4 carbon atoms in the alkyl part are preferred, and the benzyl radical and the 1-naphthylmethyl radical are particularly preferred.

Fluorine, chlorine, bromine and iodine may be mentioned as halogen, fluorine, chlorine and bromine may be preferably mentioned as halogen, and chlorine and bromine may be particularly preferably mentioned as halogen.

The alkyl, aryl and aralkyl radicals can be substituted by one or more, preferably one, two or three, particularly preferably one or two, identical or different radicals.

Halogens, such as fluorine, chlorine and bromine, isocyanate groups, cyano groups, nitro groups, carboxylate groups having 1 to 4 C atoms in the alkoxy part, alkoxy groups having 1 to 4 C atoms, such as methoxy, ethoxy, propoxy and butoxy, alkyl groups having 1 to 4 C atoms, such as methyl, ethyl, propyl, isopropyl, butyl, 2-butyl, and tert.-butyl, aralkyl groups, such as benzyl and naphthyl, and aryl groups, such as phenyl and naphthyl, may be mentioned as examples of substituents of the alkyl, aryl and aralkyl radicals. Chlorine, bromine, nitro groups, carboxylate groups, alkoxy groups, such as methoxy and ethoxy, alkyl groups, the benzyl radical and the phenyl group are preferred. Chlorine, bromine, nitro and methyl are particularly preferred substituents.

Preferred thioethers for the process according to the invention are compounds of the formula

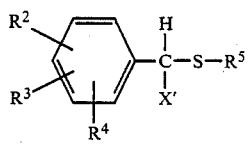     (III)

wherein

R², R³ and R⁴ are identical or different and denote hydrogen, halogen, lower alkyl, phenyl, benzyl, phenoxy or nitro, and wherein adjacent radicals can be linked to a six-membered hydrocarbon ring, X' denotes hydrogen, chlorine or bromine and R⁵ denotes a phenyl or benzyl radical which is optionally substituted by halogen, lower alkyl or nitro, the nitrile group or the group

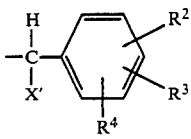

wherein
R², R³, R⁴ and X' have the meaning given above.
Thioethers of the formula

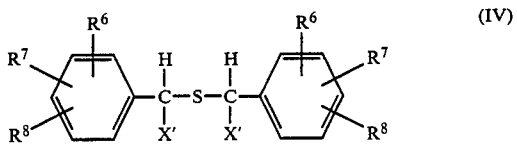

wherein
R⁶, R⁷ and R⁸ are identical or different and denote hydrogen, fluorine, chlorine, bromine, methyl, ethyl, propyl, phenyl, benzyl, phenoxy or nitro, and X' has the meaning given above,
are particularly preferred for the process according to the invention.

The following thioethers can be employed, for example, in the process according to the invention: benzyl sulphide, o,m,p-xylyl sulphide, o,m,p-bromobenzyl sulphide, o,m,p-nitrobenzyl sulphide, o,m,p-ethylbenzyl sulphide, o,m,p-phenoxy-benzyl sulphide, α,β-menaphthyl sulphide, o,m,p-xylyl thiocyanate, o,m,p-bromobenzyl thiocyanate, o,m,p-nitrobenzyl thiocyanate, o,m,p-phenoxybenzyl thiocyanate, o,m,p-xylyl phenyl thioether, o,m,p-bromobenzyl phenyl thioether, o,m,p-nitrobenzyl phenyl thioether, o,m,p-xylyl-4-chlorophenyl thioether, o,m,p-bromobenzyl-4-chlorophenyl thioether, 2-chloro-3-methylbenzyl sulphide and 4-nitro-3-chlorobenzyl sulphide.

o,m,p-Xylyl sulphide, o,m,p-bromobenzyl sulphide, o,m,p-nitrobenzyl sulphide, o,m,p-phenoxy-benzyl sulphide, α,β-methylnaphthyl sulphide, o,m,p-xylyl thiocyanate, o,m,p-bromobenzyl thiocyanate, o,m,p-nitrobenzyl thiocyanate, o,m,p-xylyl phenyl thioether, o,m,p-bromobenzyl phenyl thioether, o,m,p-xylyl-4-chlorophenyl thioether and 2-chloro-3-methyl-benzyl sulphide are preferred.

The thioethers which are employed in the process according to the invention and in which the radical X represents hydrogen can be prepared, for example, by the reaction of chloromethyl-substituted aromatic compounds with sodium sulphide (Houben-Weyl, 4th edition 1962, IX, page 97). Symmetrical thioethers are preferably prepared by this method.

Thioethers which can be employed in the process according to the invention and in which the radical X represents hydrogen can also be prepared by the reaction of chloromethyl-substituted aromatic compounds with alkali metal salts of oganic mercaptans (Houben-Weyl, 4th edition 1962, IX, page 103). Symmetrical and unsymmetrical thioethers can be prepared using this method.

Thioethers which can be employed in the process according to the invention and in which the radical X represents halogen can be prepared, according to Journal of American Chemical Society 89, 4483 (1967), by the reaction of aromatic aldehydes with organic mercaptans in the presence of hydrogen halide.

Unsymmetrical thioethers can also be employed in the process according to the invention, so that two different trichloromethyl-substituted aromatic compounds can simultaneously be prepared.

Chlorine, oxychlorides of elements of the 6th main group (periodic system according to Mendeleev), for example oxychlorides of sulphur, such as sulphuryl chloride, and chlorides of elements of the 5th main group (periodic system according to Mendeleev), for example chlorides of phosphorus, such as phosphorus pentachloride, and hypochlorous acid can be used in the process according to the invention as the chlorinating agent. Mixtures of these chlorinating agents can be employed. Chlorine is preferably employed.

2 to 12 mols, preferably 2 to 8 mols, particularly preferably 2 to 5 mols, of the chlorinating agent are employed per mol of the thioether, for each group to be chlorinated.

The chlorination by the process according to the invention can be carried out by catalytic methods, which are in themselves customary, for initiating free-radical reactions. Thus, it can be advantageous to carry out the process according to the invention in the presence of UV light. The chlorination can also be carried out with the aid of customary organic free-radical initiators, such as peroxides, for example benzoyl peroxide, and azo compounds, for example azobiisobutyric acid dinitrite, with or without the use of UV light. When present the catalysts or free radical initiators are present in an amount of 0.1 to 5 weight percent, base in the weight of the reation mixture.

Organic free-radical initiators and light, particularly preferably UV light, are preferably employed. In a preferred embodiment, the process according to the invention is carried out, with high selectivity, without a catalyst.

The process according to the invention can be carried out with or without a solvent. Inert organic solvents can be employed as the solvent. Halogenated solvents, such as chlorinated hydrocarbons, for example chloroform, carbon tetrachloride, chlorobenzene, tetrachloroethylene and dichlorobenzene, fluorinated organic solvents, for example benzotrifluoride, and oxyhalides of elements of the 5th main group, for example oxyhalides of phosphorus, such as phosphorus oxychloride, can be employed, for example, as inert organic solvents.

Chlorinated hydrocarbons, such as carbon tetrachloride, chloroform and chlorobenzene, and oxychlorides of elements of the 5th main group, such as oxychlorides of phosphorus, are preferably employed. Carbon tetrachloride and phosphorus oxychloride are particularly preferably employed. 50 to 2,000 ml, preferably 100 to 1,000 ml, particularly preferably 100 to 500 ml of solvent are employed per mol of thioether.

The process according to the invention can also be carried out in solvent mixtures.

The process according to the invention can preferably be carried out without a solvent if the thioether employed is liquid at the chosen reaction temperature.

The process according to the invention can be carried out in the temperature range of from −10° to 125° C., preferably from 10° to 110° C., particularly preferably from 20° to 100° C.

The process according to the invention can be carried out, for example, in such a manner that the thioether, and if appropriate the catalyst, are initially introduced. The halogenating agent is added to these substances.

The process according to the invention can also be carried out in such a manner that the halogenating agent is initially introduced. The thioether, if appropriate mixed with a catalyst, is added to the halogenating agent.

The process according to the invention can also be carried out in such a manner that the halogenating agent, and if appropriate the catalyst, are initially introduced. The thioether is added to these substances.

A further embodiment of the process according to the invention comprises initially introducing the catalyst. The thioether to be employed and the halogenating agent are simultaneously added to the catalyst.

The process according to the invention can furthermore be carried out in such a manner that the thioether is initially introduced. In this process, the catalyst is added during the addition of the halogenating agent.

The process according to the invention is preferably carried out in such a manner that the chlorinating agent is added to the initially introduced thioether.

In one embodiment of the process according to the invention the reactants can be saturated with hydrogen chloride gas before the beginning of the reaction.

The process according to the invention can be carried out as follows:

The thioether is heated to the reaction temperature, if appropriate in a solvent. The chlorinating agent is then added to the mixture until chlorine is no longer taken up, and this can be recognised by the cessation of HCl evolution. After the mixture has cooled to room temperature, the solvent and the sulphur chloride formed are distilled off. The reaction product which remains as a residue is purified by distillation and/or crystallisation. If, in carrying out the process according to the invention, two different trichloromethyl-substituted aromatic compounds are formed, these compounds can be purified by crystallisation and/or distillation, and can be separated if appropriate.

Trichloromethyl-substituted aromatic compounds of the process according to the invention can be converted by fluorination with hydrogen fluoride into trifluoromethylsubstituted aromatic compounds, which are intermediate products for the synthesis of plant protection agents (German Offenlegungsschrift No. 2,537,753). Fluorination can be effected in accordance with U.S. Pat. No. 4,155,940, whose disclosure is hereby incorporated herin by reference.

With the aid of the process according to the invention, one can, surprisingly, prepare trichloromethyl-substituted aromatic compounds which could not hitherto be prepared by the known process. Thus, for example, it is possible within the scope of the present invention to prepare new trichloromethyl-substituted aromatic compounds of the formula

wherein
Ar$^1$ represents a bromophenyl or a naphthyl radical which is substituted by alkyl or alkoxy having more than 2 carbon atoms, aryl, aralkyl or halogen.

In general, the new trichloromethyl-substituted aromatic compounds are substituted by 1 to 3, preferably 1 or 2, radicals. According to the invention, bromophenyl is o-, m- or p-bromophenyl, preferably m-bromophenyl.

The new trichloromethyl-substituted compounds of the formula

wherein
Ar$^2$ represents a bromophenyl or a naphthyl radical which is substituted by straight-chain or branched alkyl or alkoxy having 2 to 8 carbon atoms, phenyl, benzyl, fluorine, chlorine or bromine,
are preferred according to the invention.

The following new trichloromethyl-substituted aromatic compounds may be mentioned as individual examples: o-bromobenzotrichloride, p-bromobenzotrichloride, 2,4-dibromobenzotrichloride, 2-bromo-3-methylbenzotrichloride, 3-bromo-4-methylbenzotrichloride, 3-nitro-4-methylbenzotrichloride, 4-nitro-3-methylbenzotrichloride, o,m,p-ethylbenzotrichloride, o,m,p-phenylbenzotrichloride and o,m,p-benzylbenzotrichloride.

The benzotrihalides according to the invention can also be converted into the corresponding carboxylic acids by saponification in the presence of sulphuric acid (Houben-Weyl, Vol. 8, page 426 et seq. (1962)). In particular in this conversion step the new benzotrihalides, form highly active insecticides (German Offenlegungsschrift No. 2,926,987) which are otherwise only obtainable by means of several reaction steps.

EXAMPLE 1

100 g of m-xylyl sulphide are dissolved in 100 ml of carbon tetrachloride. After the solution has been heated to 80° C., chlorine is introduced until the chlorine is no longer taken up. The solvent and the sulphur chloride formed are distilled off in vacuo. 164 g of reaction product, which consists of 55.2% by weight of 3-methylbenzotrichloride (determined by gas chromatographic analysis), remain as the residue. Pure 3-methylbenzotrichloride of boiling point 108° to 109° C./12 mm, n$_D{}^{20}$: 1.5545, is obtained by distillation over a column.

EXAMPLE 2

300 g of m-xylyl sulphide are heated to 90° C. and saturated with dry hydrogen chloride gas. Approximately 400 g of chlorine are then introduced at this temperature. At the beginning of the reaction, the uptake of chlorine is quantitative, and chlorine escapes from the reaction mixture only towards the end of the reaction. The sulphur chloride formed is distilled off. 477 g of crude product remain, and are distilled. The distillate contains 54.2% y weight of 3-methylbenzotrichloride.

EXAMPLE 3

30 g of m-xylyl chloride are dissolved in 150 ml of carbon tetrachloride. Chlorine is introduced at 20° to 30° C., until the solution is saturated. The reaction mixture obtained after the end of the introduction of chlorine contains 51.3% by weight (determined by gas chromatographic analysis) of 3-methylbenzotrichloride.

EXAMPLE 4

30 g of m-xylyl sulphide are dissolved in 80 ml of phosphorus oxychloride. After the solution has been heated to 70° to 75° C., chlorine is introduced until the solution is saturated. After the solvent and the resulting sulphur chloride have been distilled off, 20 g of 3- methylbenzotrichloride are isolated after distillation of the reaction mixture obtained.

EXAMPLE 5

Example 4 is repeated with chlorobenzene instead of phosphorus oxychloride as the solvent. 22.8 g of 3-methylbenzotrichloride are obtained.

EXAMPLE 6

520 g of p-xylyl sulphide are dissolved in 500 ml of carbon tetrachloride. Chlorine is introduced at the reflux temperature of the solution until the latter is saturated. After the solvent and the resulting sulphur chloride have been distilled off, the reaction product obtained is distilled. 430 g of 4-methylbenzotrichloride of boiling point 104° to 105° C./9 mm are obtained, and this product solidifies to crystals at 46° C.

EXAMPLE 7

200 g of o-xylyl sulphide are reacted as described in Example 6. 105 g of 2-methylbenzotrichloride of boiling point 108° to 110° C./11 mm, $n_D^{20}$: 1.5655, are obtained.

EXAMPLE 8

100 g of 1-naphthyl methyl sulphide are dissolved in 250 ml of carbon tetrachloride. Chlorine is introduced into the solution at 75° to 80° C., until the solution is saturated. The solvent and the resulting sulphur chloride are then distilled off. 30 g of 1-trichloromethyl-naphthalene of boiling point 124° to 128° C./0.3 mm are obtained, after fractional distillation, from the reaction product which remains as a residue.

EXAMPLE 9

Bis-(4-nitrobenzyl) sulphide is dissolved in 300 ml of phosphorus oxychloride. 300 g of chlorine are introduced at 70° to 80° C. during the course of 1 hour. After the mixture has been cooled to approximately 20° C., chlorine is again introduced for 30 minutes. After the sulphur chloride has been distilled off, the crude product thus obtained is purified by distillation. 209 g of 4-nitrobenzotrichloride of boiling point 115° to 118° C./0.1 mm are obtained, and this product solidifies to crystals at 42° to 44° C.

EXAMPLE 10

20 g of m-xylyl thiocyanate are dissolved in 100 ml of phosphorus oxychloride. Chlorine is introduced (for approximately 8 hours) at the reflux temperature of the solution, until the solution is saturated. After the end of the introduction of chlorine, a content of 50.5% by weight of 3-methylbenzotrichloride is established by means of gas chromatographic analysis.

EXAMPLE 11

150 g of 4-chlorophenyl 4-methylbenzyl thioether are dissolved in 200 ml of carbon tetrachloride. Chlorine is introduced at 80° C. until the solution is saturated. After the end of the reaction, 85 g of 4-methylbenzotrichloride are obtained after distillation over a column.

EXAMPLE 12

48 g of o-xylyl sulphide are dissolved in 100 ml of carbon tetrachloride. 200 g of sulphuryl chloride are added dropwise to the solution at 60° C. After the end of the addition, the mixture is further stirred at this temperature for 5 hours. After working up the mixture by distillation, 21 g of 2-methylbenzotrichloride are obtained.

EXAMPLE 13

80 g of 2-bromobenzyl thioether are dissolved in 200 ml of carbon tetrachloride. Chlorine is introduced at 75° C., until the solution is saturated. After the mixture has cooled to 20° C., chlorine is again introduced for 30 minutes. The reaction mixture is then distilled at 0.5 mm. 36 g of 2-bromobenzotrichloride (30% of theory) are obtained at a pass-over temperature of 82° to 88° C./0.5 mm.

EXAMPLE 14

121 g of m-xylyl sulphide are dissolved in 250 ml of carbon tetrachloride. 220 g of chlorine are introduced, at 20° C. and with simultaneous irradiation with UV light, during the course of 4 hours. After the solvent has been distilled off, 190g of crude product remain, containing 34% by weight of 3-methylbenzotrichloride, according to gas chromatographic analysis.

EXAMPLE 15

50 g of 4-methoxy-α-chlorobenzyl 4-chlorophenyl thioether are dissolved in 50 ml of carbon tetrachloride. The introduction of chlorine is started at 25° C. Chlorine is introduced until the solution is saturated, the temperature of the reaction mixture increasing to 50° C. during the introduction of the chlorine. After the uptake of chlorine has ended, the solvent is distilled off and the residue is crudely distilled. Passover temperature: 105° to 165° C./20 mbar. 60 g of distillate are obtained, containing 17.4% by weight of 4-methoxybenzotrichloride according to gas chromatographic analysis.

EXAMPLE 16

4-Chlorophenyl 4-methylbenzyl thioether 150 g of 4-chlorothiophenol in 200 ml of water, 65 g of potassium hydroxide, 10 g of tetraethylammonium chloride and 140 g of 4-methylbenzyl chloride are initially introduced into a stirred apparatus and are heated under reflux for 4 hours. 300 ml of water are then added, and the mixture is cooled. The solid product is filtered off under suction and washed with water. After the crystals have been dried, 230 g of product of melting point 72° to 73° C. remain.

EXAMPLE 17

4-Methoxy-α-chlorobenzyl 4-chlorophenyl thioether 144 g of 4-chlorothiophenol in 300 ml of methylene chloride are initially introduced, and 136 g of 4-methoxybenzaldehyde in 300 ml of methylene chloride are added. After the addition of 80 g of calcium chloride, dry hydrogen chloride is introduced into the mixture for 6 hours. After the mixture has stood overnight, it is filtered and the methylene chloride solution is concentrated. The solid product is recrystallised from petroleum ether. 210 g of crystals of melting point 76° to 77° C. are obtained.

EXAMPLE 18 m-Xylyl sulphide 650 g of 3-methylbenzyl chloride are initially introduced into 900 ml of methanol under reflux, and 585 g of sodium sulphide monohydrate, dissolved in 450 ml of water, are added dropwise to the mixture during the course of 1 hour. After the end of the addition, the mixture is further stirred under reflux for 5 hours, and is then cooled and diluted with 2,000 ml of water. The organic phase is separated off with methylene chloride, and is distilled after having been dried. 495 g of m-xylyl sulphide are obtained at a pass-over temperature of 142° to 145° C./0.25 mm.

EXAMPLE 19 o-Xylyl sulphide

The experiment is carried out as in Example 18. Yield 92% (of theory) of melting point 86° to 88° C.

EXAMPLE 20 p-Xylyl sulphide

The experiment is carried out as in Example 18. Yield 97% (of theory) of melting point 75° to 76° C.

EXAMPLE 21

4-Nitrobenzyl sulphide

The experiment is carried out as in Example 18. Yield 94% (of theory) of melting point 157° to 159° C.

EXAMPLE 22

1-Naphthylmethyl sulphide

The experiment is carried out as in Example 18. 88% (of theory) of melting point 104° to 106° C. is obtained.

EXAMPLE 23

2-Bromobenzyl sulphide

The experiment is carried out as in Example 18. 94% (of theory) of melting point 62° to 63° C. is obtained.

EXAMPLE 24

595 g of 3-nitro-4-methylbenzyl sulphide are initially introduced into 1,000 ml of trichloromethane at the reflux temperature, and the mixture is reacted with chlorine until saturation occurs. Chlorine is then introduced for a further 1 hour at 20° C., and is subsequently expelled with nitrogen. 315 g of 3-nitro-4-methylbenzotrichloride are obtained by fractional distillation at a boiling point of 128°-130° C./2.5 mbar.

The 3-nitro-4-methylbenzyl sulphide employed was obtained from 3-nitro-4-methylbenzyl chloride, analogously to Example 21.

EXAMPLE 25

By introducing chlorine into a solution of 80 g of 3-methyl-4-nitrobenzyl sulphide in 150 ml of trichloromethane under reflux, until the solution is saturated, 115 g of crude reaction product is obtained (after the solvent has been distilled off), which consists of 55.5% of 3-methyl-4-nitrobenzotrichloride according to gas chromatographic analysis.

The 3-methyl-4-nitrobenzyl sulphide employed was obtained from 3-nitro-4-methylbenzyl chloride, analogously to Example 21.

The following examples were carried out in an analogous manner to that of Example 18:

| Example No. | Starting compound | Reaction product | Boiling point °C. | Melting point °C. | Refractive index $n_D^{20}$ |
|---|---|---|---|---|---|
| 26 | (2-Cl, 3-CH3-benzyl)2S | 2-Cl-3-CH3-benzotrichloride | 142–145° C. at 16 mbar | 56–58° C. | |
| 27 | (3-Cl, 5-CH3-benzyl)2S | 3-Cl-4-CH3-benzotrichloride | 139–142° C. at 20 mbar | 42–44° C. | |
| 28 | 3-ethylbenzyl phenyl sulphide | 3-ethyl-benzotrichloride | 151–155° C. at 12 mbar | | 1.5488 |
| 29 | (2-Br, 4-Cl-benzyl)2S | 2-Br-4-Cl-benzotrichloride | 133–135° C. at 0.4 mbar | | 1.6363 |

| Example No. | Starting compound | Reaction product | Boiling point °C. | Melting point °C. | Refractive index $n_D^{20}$ |
|---|---|---|---|---|---|
| 30 | | | 105–110° C. at 0.2 mbar | | 1.6185 |
| 31 | | | 88–90° C. at 1.5 mbar | | 1.5994 |
| 32 | | | 100–105° C. at 0.25 mbar | | 1.5640 |

What is claimed is:

1. A process for the preparation of a trichloromethyl-substituted aromatic compound of the formula Ar—CCl$_3$ wherein
Ar is a member of the group consisting of unsubstituted aryl radicals having 6 to 14 C-atoms and aryl radicals having 6 to 14 C-atoms substituted independently from each other by 1 to 3 radicals of the group consisting of fluorine-, chlorine-, bromine-, isocyanate-, cyano-, nitro-, C$_1$- to C$_4$-carboxylate-, C$_1$- to C$_4$-alkoxy-, C$_1$- to C$_4$-alkyl-, benzyl, naphthyl- and phenyl groups,
which comprises contacting a thioether of the formula

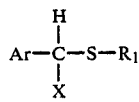

wherein
Ar has the above mentioned meaning,
X is selected from the group consisting of hydrogen and halogen, and
R$_1$ is Ar as defined above, with chlorine, at a temperature in the range of −20° C. to +125° C.

2. A process according to claim 1, wherein the process is carried out in the absence of a solvent employing thioether which is liquid at the reaction temperature.

3. A process according to claim 1, wherein the process is carried out in the presence of a solvent.

4. A process according to claim 1, wherein the process is carried out in the presence of a catalyst.

5. A process according to claim 1, wherein the process is carried out in the presence of an organic free-radical initiator and in the presence of UV light.

6. A process according to claim 1, wherein the reactants are saturated with hydrogen chloride before commencement of the reaction.

* * * * *